United States Patent [19]

Puschel et al.

[11] 4,301,243

[45] Nov. 17, 1981

[54] PHOTOGRAPHIC RECORDING MATERIAL

[75] Inventors: Walter Puschel; Heinrich Odenwalder; Erwin Ranz, all of Leverkusen, Fed. Rep. of Germany

[73] Assignee: AGFA-Gevaert Aktiengesellschaft, Leverkusen, Fed. Rep. of Germany

[21] Appl. No.: 103,000

[22] Filed: Dec. 12, 1979

[30] Foreign Application Priority Data

Dec. 23, 1978 [DE] Fed. Rep. of Germany ....... 2855997

[51] Int. Cl.$^3$ .................... G03C 1/40; G03C 1/48; G03C 1/10; G03C 1/06
[52] U.S. Cl. .................................. 430/613; 430/214; 430/219; 430/544; 430/564; 430/607; 430/611; 430/957
[58] Field of Search ............... 430/214, 219, 505, 544, 430/607, 611, 613, 957, 564

[56] References Cited

U.S. PATENT DOCUMENTS

| 3,227,551 | 1/1966 | Barr et al. | 430/957 |
| 3,364,022 | 1/1968 | Barr | 430/957 |
| 3,379,529 | 4/1968 | Porter et al. | 430/957 |
| 3,620,746 | 11/1971 | Barr | 430/505 |
| 3,620,747 | 11/1971 | Marchant et al. | 430/505 |
| 3,930,863 | 1/1976 | Shiba et al. | 430/957 |
| 3,961,963 | 6/1976 | Shiba et al. | 430/957 |
| 4,055,429 | 10/1977 | Holmes et al. | 430/505 |

Primary Examiner—Richard L. Schilling
Attorney, Agent, or Firm—Connolly & Hutz

[57] ABSTRACT

Traces of free inhibitors for the development of silver halide which might be present as impurities of inhibitor releasing compounds or which might be prematurely released therefrom because of insufficient stability thereof during storage of the photographic material are scavenged by compounds which are capable of binding free inhibitors at pH values below 7 but to a much less extent at pH values higher than 9.

4 Claims, No Drawings

PHOTOGRAPHIC RECORDING MATERIAL

This invention relates to a photographic recording material comprising at least one light-sensitive silver halide emulsion layer and at least one layer containing a compound which is capable of releasing development inhibitors on development and contains at least one other compound cabable of binding development inhibitors.

It is known to use so-called development inhibitor releasing compounds in photographic processes for selectively controlling the development of photographic silver halide emulsion layers. The use of development inhibitor releasing compounds can substantially improve the sensitometric properties of the photographic materials and the structure of the image, by reducing contrast and producing special development effects. Further information on this subject may be found in the article "Development-Inhibitor-Releasing (DIR) Couplers in Color Photography" in Photographic Science and Engineering, Volume 13, page 74 (1969). The use of development inhibitor releasing couplers, hereinafter referred to as DIR couplers, which are capable of reacting with the oxidation products of colour developer compounds to release a development inhibitor has already been disclosed, e.g. in U.S. Pat. No. 3,148,062. In U.S. Pat. No. 3,379,529, for example, the use of certain developer compounds which release development inhibitors as a result of development of the silver halide has been disclosed. Other development inhibitor releasing compounds which are capable of releasing development inhibitors imagewise in an anionic form have been described, for example, in U.S. Pat. Nos. 3,297,445; 3,227,554; 617,291 and 3,632,345. By release of these inhibitors during development it is possible to reduce the graininess, improve the sharpness of the developed image and control the gradation and sensitivity of the silver halide emulsion. It is also known that when certain substances are added to a photographic material, they release development inhibitors in a non-imagewise distribution under the conditions of photographic development; in many cases this has an advantageous effect on fogging. It is relevant to mention in this connection, for example, U.S. Pat. No. 3,819,379, in which the inhibitors are added in a complex form, or U.S. Pat. No. 3,615,617, in which the inhibitor is used as a derivative carrying a blocked mercapto group.

It is often desirable to restrict the area of action of inhibitors in order to ensure that they will not migrate into other layers than those in which they were liberated and impair development there or even migrate out of the material into the developer solution, as this would deleteriously affect subsequent development results. This applies both to inhibitors which are released imagewise and those which are released in a uniform distribution. For this purpose, it is known to restrict the range of action of these inhibitors by equipping the photographic material with layers which are capable of binding the development inhibitors. Such "scavenger layers" for development inhibitors have been disclosed, for example, in British Pat. No. 1,201,110. In this Patent there is described, for example, a color photographic recording material in which an intermediate layer containing silver halide grains of comparatively low sensitivity to light is placed between two silver halide emulsion layers of normal sensitivity. One of the aforesaid silver halide emulsion layers contains a cyan coupler having a bromine or iodine atom in the coupling position, from which bromide or iodide ions are released as development inhibitors in the process of color development. The intermediate layer of comparatively low light sensitivity binds the diffusing development inhibitors by absorption and thus protects the other emulsion layers from the development inhibitors or development inhibitor fragments. According to U.S. Pat. No. 3,737,317, Lippmann emulsions are arranged as covering or separating layers either above, between or below image-producing silver halide emulsion layers in order to prevent development inhibitors migrating between the layers or leaving the photographic material to enter the developer solution. One disadvantage of using such covering or separating layers with fine grained silver halide, however, is that these layers frequently alter the sensitometric properties of the image-producing layer. Such an alteration is particularly undesirable when the Lippmann emulsion is used as scavenger layer for development inhibitors between two image-producing layers, particularly in fine grained photographic materials. The use of inhibitor-absorbing colloid layers containing a polymer which is capable of absorbing the development inhibitors has been disclosed in German Offenlegungsschrift No. 2,448,232. All of the substances mentioned for binding diffusing development inhibitors are effective in the alkaline pH range of developer baths, i.e. under the usual conditions for releasing development inhibitors either imagewise or in uniform distribution. The effect of the known inhibitor receptors therefore counteracts the effect of the inhibitor releasing compounds.

The use of inhibitor releasing compounds and particularly of DIR couplers or DIR developers may give rise to difficulties if they still contain traces of free inhibitors from their preparation, which are difficult to remove under usual conditions of synthesis. Such compounds are not always completely stable under the conditions of storage of the finished photographic material. Traces of free inhibitors are liable to have a deleterious effect on the sensitometric properties of the layers. The substances described above for binding free inhibitors are not capable of overcoming this disadvantage since they act in the alkaline pH range, i.e. precisely under the conditions in which the occurrence of free inhibitors is desirable.

It is an object of the present invention to provide measures by which unwanted traces of free inhibitors can be rendered ineffective but which do not impair the activity of the DIR compounds when the material is subsequently processed in the photographic process.

It has now been found that a protection can be obtained by using compounds which are capable of binding inhibitors at a slightly acid or neutral pH (pH below 7) but not or only very much more slowly at the higher pH values of photographic development (pH 9–13) if these compounds are added to the layers containing the inhibitor releasing compounds. It is assumed that these compounds are capable of reacting with those groups in the inhibitors which are responsible for the inhibitory action and block these groups. The inhibitors used are preferably heterocyclic mercapto compounds, and more preferably such compounds which contain a mercapto group on a ring carbon atom adjacent to a ring nitrogen atom.

The present invention relates to a photographic recording material comprising at least one silver halide emulsion layer and at least one layer containing a non-diffusible compound which is capable of releasing a diffusible development inhibitor under the condition of the alkaline development of the silver halide. The photographic material is characterised in that the layer which contains the non-diffusible, inhibitor releasing compound also contains another compound which is capable of binding free inhibitors at pH values below 7, but cannot do so or only to a much less extent at pH values between 9 and 13.

Compounds suitable for this purpose correspond, for example, to the following general formula I

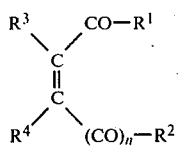

in which
R¹ and R² represent each individually hydrogen, or a substituent selected from the group consisting of alkyl groups such as methyl, ethyl, isobutyl, dodecyl, octadecyl; aryl groups such as phenyl; hydroxyl; alkoxy groups such as methoxy, ethoxy, butoxy; —NR-alkyl and —NR-aryl groups, wherein R represents hydrogen or alkyl; or both R¹ and R² together complete a 5- or 6-membered carbocyclic or heterocyclic ring such as a p-quinone ring, a δ-pyrone ring or a maleic imide ring;
R³ and R⁴ represent each individually hydrogen or a substituent selected from the group consisting of alkyl groups preferably having up to 18 carbon atoms; alkoxy groups such as methoxy, ethoxy, butoxy; aryl groups such as phenyl; halogen atoms such as chlorine, alkoxy carbonyl groups such as ethoxy carbonyl; and cyano
$n = 0$ or 1, preferably $n = 1$ when R¹ and R² complete a ring.

The alkyl groups mentioned above where not otherwise stated may be short chain alkyl groups such as of a carbon number of 1 to 6 or longer chain alkyl groups of up to 18 carbon atoms, they may be straight chain or branched alkyl groups and they may carry further substituents such as phenyl, halogen or alkoxy groups.

Formula I as represented above does not necessarily mean that the compounds described above must be in the cis-configuration. In the case of acyclic compounds, one would generally assume that they are predominantly, or even completely, in the form of the trans-isomers.

The compounds preferably contain a diffusion resistance conferring group in one of the groups R¹, R², R³ and R⁴ or in the group formed by R¹ and R² to complete a ring. Diffusion resistance conferring groups are groups which make it possible for the compounds used according to the invention to be incorporated in diffusion resistant form in the hydrophilic colloids normally used in photographic materials. Organic groups generally containing straight chain or branched chain aliphatic groups and optionally also containing carbocyclic or heterocyclic, optionally aromatic groups with, generally, 8 to 20 carbon-atoms are preferred. These groups are attached to the remainder of the molecule either directly or indirectly, e.g. through one of the following groups: NHCO, NHSO₂, NR (R represents hydrogen or alkyl), —O— or —S—. The diffusion resistance conferring group may also contain water-solubilising groups, e.g. sulfo groups or carboxyl groups, and these may also be present in an anionic form. As the properties as regards diffusibility depend on the molecular size of the total compound, it may sufficient in certain cases to use groups of shorter chain length as "diffusion resistance-conferring groups" such as tertiary butyl, isoamyl or tertiary amyl groups, for example when the compound of the invention is incorporated into the layer using so-called oil formers or highly-boiling coupler solvents. The compounds according to the invention however, need not have absolute resistance to diffusion in the present case since they would not be expected to have any deleterious effect on the other layers of the photographic material. It is sufficient to restrict the diffusion of the compounds according to the invention to such an extent that the quantity of compound according to the invention left in the original layer after the usual storage time of the photographic material is sufficient to inactivate inhibitors which are released there under storage conditions.

The compounds according to the invention also include polymers containing structural units of the above formula I attached to a given polymer structure through one of the substituents, preferably through R¹. Suitable polymer structures include, for example, copolymers of maleic acid anhydride or itaconic acid anhydride with copolymerisable monomers such as vinyl methyl ethers or styrene, or copolymers of N-oxoalkylacrylamides.

The following are examples of suitable compounds according to the invention:

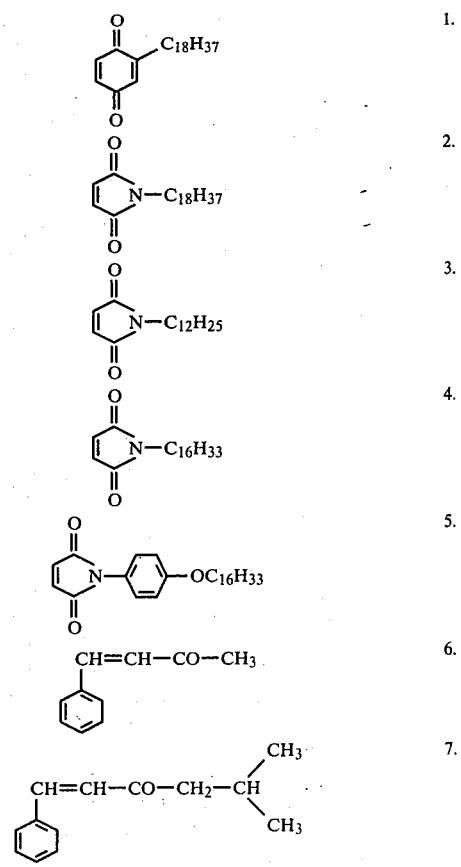

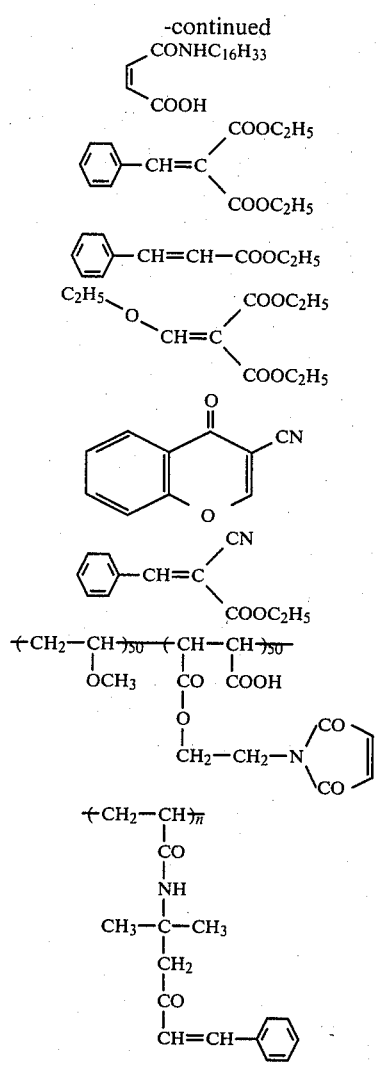

Preparation of the compounds according to the invention is easily carried out by known methods and is exemplified below in the preparation of some of the compounds according to the invention.

Preparation of Compound 1

3.3 g of sodium dichromate are added portionwise with stirring to 12 g of octadecylhydroquinone suspended in 160 ml of glacial acetic acid. 300 ml of water are added after 1.5 hours. The resulting precipitate is suction filtered and dissolved in 70 ml of chloroform. The reaction mixture is filtered after the addition of Fuller's earth, and octadecylbenzoquinone is precipitated from the filtrate by the addition of 200 ml of methanol with cooling. 8.5 g of the compound having a melting point of 94° to 95° C. are obtained.

Preparation of Compound 4

1st Stage 19.6 g of maleic acid anhydride are dissolved in 500 ml of toluene at 90° C. The temperature is maintained at 90° C. while 48.2 g of hexadecylamine, dissolved in 200 ml of toluene are added dropwise within 45 minutes. After one more hour at 90° C. followed by cooling, the resulting precipitate is suction filtered and washed with methanol. 44.5 g of N-hexadecylmaleic amide melting at 101° to 102.5° C. are obtained.

2nd Stage 16.95 g of the compound obtained in the 1st Stage are heated under reflux with 2.05 g of sodium acetate in 20 ml of acetic acid anhydride for 30 minutes. The reaction mixture is poured into 100 ml of water. The semi-solid precipitate which forms is taken up in chloroform and the chloroform solution is stirred up with Fuller's earth and then filtered, and the filtrate is concentrated by evaporation. The residue is stirred up with 400 ml of 90% methanol, suction filtered and washed with 90% methanol. 10.7 g of N-hexadecylmaleic imide melting at 46° to 49° C. are obtained.

Polymeric compounds according to the invention are suitably prepared from polymers containing functional side groups which are reacted with suitable reactive groups of a compound having the structure of the given formula I. Polymers having maleic acid anhydride or itaconic acid anhydride units may be converted into the corresponding polymeric semi-esters (Compound 14) by reaction with monomers of formula I containing hydroxyl groups in accordance with the method given in Houben-Weyl, Methoden der Organischen Chemie, Vol. XIV/2, page 736. Polymers carrying an activated methylene group in a side chain adjacent to a carbonyl group may be reacted with aromatic aldehydes (Compound 15) by the process described in German Auslegeschriften Nos. 1,042,231 and 1,052,688. The polymers according to the invention have molecular weights in the range of 5000 to 200,000.

The compounds according to the invention are particularly effective as inhibitor receptors if they are directly added during preparation of a coupler emulsion which contains impurities of free inhibitor or which, as a result of insufficient stability, releases small quantities of unwanted inhibitor during storage or at elevated temperatures.

As already mentioned above, the compounds according to the invention are added to that layer of the photographic material which also contains the non-diffusible inhibitor releasing compound. The compounds according to the invention are incorporated in the layer by the usual methods. For example, any water-solubilizing groups present may be used to introduce the compounds into the casting solution from aqueous alkaline solutions. If the compounds are hydrophobic, they may be incorporated in the layer by one of the known emulsification processes. Such processes have been described, for example, in British Pat. Nos. 791,219 and 1,099,414 to 1,099,417. It is also possible to prepare aqueous dispersions of the compounds according to the invention and add them to the casting solutions. The compounds according to the invention and the non-diffusible inhibitor releasing compounds may be added to the casting solutions either simultaneously or successively. The optimum quantity of compound according to the invention may vary within relatively wide limits. The most suitable concentration can be determined by simple tests. The quantity added is generally calculated so that the quantity of compound according to the invention present in the layer is 1 mg to 1 g/m², preferably 2 mg to 100 mg/m². It is particularly suitable to use quantities in the range of 5 to 50% by weight, based on the quantity of the inhibitor releasing compound.

The photographic materials according to the invention are preferably color photographic recording materials containing several silver halide emulsion laters differing in their spectral sensitivity. One of the silver halide emulsion layers is generally sensitive to blue light, another to green light and a third to red light. Each of these layers has a color coupler associated with it to produce a partial color image, the color of which is generally complementary to the color of light to which the associated silver halide emulsion layer is sensitive. The aforesaid light-sensitive layers may also consist of two of more partial layers.

In the color photographic material according to the invention, a non-diffusible compound capable of releasing a development inhibitor under the conditions of the photographic development by the influence of the developer alkali is associated with at least one of the aforesaid light-sensitive silver halide emulsion layers. The released development inhibitors may be, for example, heterocyclic mercapto compounds, derivatives of benzotriazole or bromide or iodide ions. They are preferably compounds containing a heterocyclic ring in which a mercapto group is attached to a carbon atom adjacent to a ring nitrogen atom, e.g. 5-mercapto-1-phenyltetrazole. The non-diffusible development inhibitor releasing compounds are preferably compounds from which the development inhibitor is released imagewise as a result of a reaction with color developer oxidation products. In this preferred case, development therefore takes place with a color developer compound which is preferably a derivative of p-phenylene diamine having at least one primary amino group.

By "association" and "associated" is meant that the silver halide emulsion is so arranged in relation to the color coupler and/or non-diffusible development inhibitor releasing compound and compound according to the present invention, that an interaction between them can take place in such a manner that there is an imagewise correspondence between the silver image produced and the imagewise distribution of the resulting dye or as the case may be of the released development inhibitor. The association is preferably provided by placing the said compounds (coupler, DIR compound and compound according to the present invention) in the silver halide emulsion layer itself, although they may also be present in an adjacent, light-insensitive layer. Thus, for example, the color coupler may be present in the light-sensitive silver halide emulsion layer while the DIR compounds and the compound according to the present invention which binds the free inhibitor may be present in a light insensitive layer of binder adjacent to the silver halide emulsion layer. The compounds according to the invention are also effective when they are emulsified alone in photographic layers in which free inhibitors are undesirably released from homogeneously distributed hydrophilic layer additives during storage.

Examples

The mode of action of the inhibitor acceptors according to the invention is illustrated below with reference to the following color photographic material. The quantities indicated are based on 1 m².

A red sensitive layer consisting of a high sensitivity red sensitized silver iodobromide emulsion containing 10 mol % of Ag I (30%) and a less sensitive red sensitized silver iodobromide emulsion containing 5 mol % of Ag I (70%) from 4.0 g AgNO₃ and 790 mg of a cyan coupler corresponding to the following formula

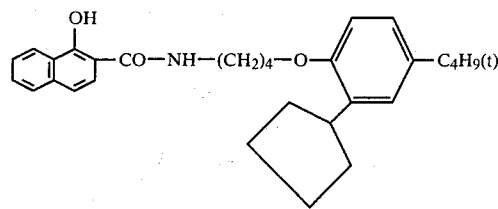

and 1.6 g of gelatin is cast on a transparent film substrate of polyethylene terephthalate.

Over this a protective layer of 0.7 g of gelatin is applied.

The material is hardened with a sulfobetaine carbodiimide corresponding to the following formula

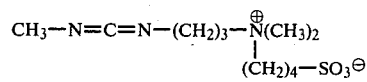

In one part of the test, 25 mg of a DIR coupler corresponding to the following formula

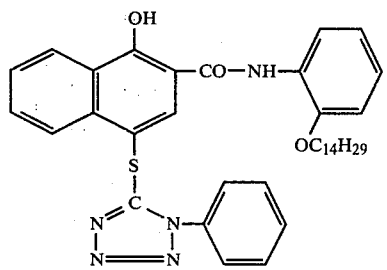

are added to the red sensitive layer. This DIR coupler is emulsified according to the following method: A solution of 10 g of DIR coupler in 10 g of dibutylphthalate, 30 ml of ethyl acetate and 5 g of dimethylformamide is emulsified in a solution of 100 ml of a 5% aqueous gelatin solution and 0.8 g of a wetting agent, e.g. a sulfonated paraffin hydrocarbon, by intensive mixing in a mixing siren.

In cases where the inhibitor receptor according to the invention and/or the free inhibitor (1-phenyl-5-mercaptotetrazole) is added to the emulsion of DIR coupler, they are dissolved together with the DIR coupler before the emulsion is prepared.

The cast samples were exposed to red light behind a grey continuous wedge and treated by a photographic process as described in "The British Journal of Photography", July 1974, pages 597 and 598.

The fog, the sensitivity at 0.2 density units above fog and the $\gamma$ values $\gamma_1$ and $\gamma_2$ at gradation sections ($\gamma_1$ from light sensitivity point to an exposure value higher by 0.8 logI.t units; $\gamma_2$ from the end of $\gamma_1$ to an exposure value higher by a further 0.8 logI.t units) are obtained from the color density curves. The results are shown in the following Table.

TABLE

| Sample | DIR coupler | Free inhibitor | Inhibitor acceptor | No. | Sensitivity | $\gamma_1/\gamma_2$ | Fog |
|---|---|---|---|---|---|---|---|
| 1 | — | — | — | | 35.7 | 1.22/0.50 | 0.22 |
| 2 | 25 mg | — | — | | 32.7 | 0.50/0.55 | 0.19 |
| 3 | " | — | 5 mg | I | 32.6 | 0.51/0.56 | 0.19 |

TABLE-continued

| Sample | DIR coupler | Free inhibitor | Inhibitor acceptor | No. | Sensitivity | $\gamma_1/\gamma_2$ | Fog |
|---|---|---|---|---|---|---|---|
| 4 | " | 0.25 mg | — | | 31.7 | 0.44/0.48 | 0.16 |
| 5 | " | " | 5 mg | 1 | 32.5 | 0.51/0.54 | 0.19 |
| 6 | " | " | " | 2 | 32.8 | 0.49/0.54 | 0.18 |
| 7 | " | " | " | 3 | 32.7 | 0.52/0.54 | 0.20 |
| 8 | " | " | " | 4 | 32.6 | 0.50/0.56 | 0.19 |
| 9 | " | " | " | 5 | 32.5 | 0.49/0.53 | 0.17 |
| 10 | " | " | " | 7 | 33.0 | 0.53/0.56 | 0.20 |
| 11 | " | — | " | 2 | 32.7 | 0.50/0.52 | 0.19 |
| 12 | " | — | " | 3 | 32.7 | 0.53/0.52 | 0.19 |
| 13 | " | — | " | 4 | 32.5 | 0.52/0.56 | 0.17 |
| 14 | " | — | " | 5 | 32.5 | 0.50/0.51 | 0.18 |
| 15 | " | — | " | 7 | 32.9 | 0.51/0.57 | 0.20 |

The gradation ($\gamma_1$), sensitivity and fog are lowered by the addition of DIR couplers (Samples 1 and 2). In Sample 4, contamination of the DIR coupler with 1% of free inhibitor (1-phenyl-5-mercaptotetrazole) has an undesirable effect of lowering the sensitivity and gradation below those of Sample 2. The addition of inhibitor acceptor to the DIR coupler emulsion contaminated with free inhibitor in samples 5 to 10 prevents the inhibitory action of the free inhibitor (Sample 4) so that these samples regain the sensitometric data of Sample 2 which is not contaminated with free inhibitor. The inhibitor receptors have virtually no effect on the sensitometric data when no contamination with free inhibitor is present, as demonstrated by samples 3 and 11 to 15.

We claim:

1. A photographic recording material comprising at least one light-sensitive silver halide emulsion layer and containing in at least one layer a nondiffusible compound which is capable of releasing a diffusible development inhibitor under the conditions of alkaline development of silver halide,
wherein the improvement comprises said non-diffusible compound containing layer contains a non-diffusible development inhibitor releasing compound which releases mercapto development inhibitors and contains a scavenging compound which is capable of binding free mercapto development inhibitor at pH values below 7 but is capable of scavenging free mercapto development inhibitor to a much less extent at pH values from 9 to 13 and wherein the scavenging compound corresponds to the following formula

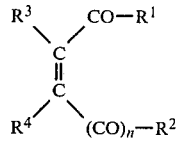

in which
R$^1$ and R$^2$ represent each individually hydrogen or a substituent selected from the group consisting of alkyl groups, aryl groups, hydroxy, alkoxy groups, —NR-alkyl and —NR-aryl groups, wherein R represents hydrogen or alkyl; or both R$^1$ and R$^2$ together complete a 5-or 6-membered carbocyclic or heterocyclic ring;
R$^3$ and R$^4$ represent each individually hydrogen or a substituent selected from the group consisting of alkyl groups, alkoxy groups, aryl groups, halogen atoms, alkoxy carbonyl groups and cyano;
n=0 or 1.

2. A photographic material as claimed in claim 1 wherein the scavenging compound contains a diffusion resistance-conferring group in at least one of the substituents R$^1$, R$^2$, R$^3$ and R$^4$ and is present in the non-diffusible compound containing layer in a non-diffusible form.

3. A photographic material as claimed in claim 1 wherein R$^1$ and R$^2$ together complete a p-quinone ring or maleic imide ring (n=1).

4. A photographic material as claimed in claim 1 wherein the non-diffusible compound which releases a development inhibitor and the scavenging compound are contained in a light-sensitive silver halide emulsion layer.

* * * * *